United States Patent [19]

Acosta et al.

[11] Patent Number: 5,700,262

[45] Date of Patent: Dec. 23, 1997

[54] BIPOLAR ELECTRODE WITH FLUID CHANNELS FOR LESS INVASIVE NEUROSURGERY

[75] Inventors: George M. Acosta, Long Beach; Lance Kumm, Tustin, both of Calif.

[73] Assignee: Neuro Navigational, L.L.C., San Diego, Calif.

[21] Appl. No.: 543,604

[22] Filed: Oct. 16, 1995

[51] Int. Cl.$^6$ .................................................. A61B 17/39
[52] U.S. Cl. ....................................... 606/48; 606/50
[58] Field of Search ............................ 606/48, 50, 46

[56] References Cited

U.S. PATENT DOCUMENTS

| | | | |
|---|---|---|---|
| 3,858,586 | 1/1975 | Lessen | 128/303.1 |
| 4,043,342 | 8/1977 | Morrison, Jr. | 128/303.14 |
| 4,126,137 | 11/1978 | Archibald | 128/303.14 |
| 4,532,924 | 8/1985 | Auth et al. | 606/50 |
| 4,565,200 | 1/1986 | Cosman | 128/642 |
| 4,674,499 | 6/1987 | Pao | 128/303.14 |
| 4,682,596 | 7/1987 | Bales et al. | 128/303.14 |
| 4,805,616 | 2/1989 | Pao | 128/303.17 |
| 4,966,597 | 10/1990 | Cosman | 606/50 |
| 5,009,656 | 4/1991 | Reimels | 606/48 |
| 5,013,312 | 5/1991 | Parins et al. | 606/37 |
| 5,085,659 | 2/1992 | Rydell | 606/50 |
| 5,089,002 | 2/1992 | Kirwan, Jr. | 606/50 |
| 5,207,684 | 5/1993 | Nobles | 606/108 |
| 5,250,047 | 10/1993 | Rydell | 606/48 |
| 5,277,696 | 1/1994 | Hagen | 606/50 |
| 5,281,216 | 1/1994 | Klicek | 606/42 |

OTHER PUBLICATIONS

Article: A Bipolar Electrode for Vascular Electrocoagulation with Alternating Current. Francis Brunelle and others. Radiology vol. 137. pp. 239–240. Oct. 1990.
Article: The Mechanism of Blood Vessel Closure By High Frequency Electrocoagulation. Sigel and Dunn. Surgery, Gynecology & Obstetrics. pp. 823–831. Oct. 1965.
Article: Experimental Closure of Arteriovenous Fistula by Transcatheter Electrocoagulation. Phillips and others. Diagnostic Radiology, vol. 115, pp. 319–321. May 1975.
Article: Ambulatory Stab Evulision Phlebectomy For Truncal Varicose Veins. Goren and Yellen. The American Journal of Surgery, vol. 162, pp. 166–174. Aug. 1991.
Article: Catheter for Endoluminal Bipolar Electrocoagulation. Christoph D. Becker and others. Radiology. vol. 170, pp. 561–562. 1989.
Article: Electrothrombosis as a Treatment of Cirsoid Angioma in the Face and Scalp and Varicose of the Leg. Ogawa and Inoue. Plastic and Reconstructive Surgery. pp. 310–318. Sep. 1982.
Article: Vessel Occlusion with Transcatheter Electrocoagulation: Initial Clinical Experience. Thompson and others. Diagnostic Radiology, vol. 133, pp. 335–340. Nov. 1979.
Article: Technical Use of Transcatheter Electrocoagulation. Miller and others. Work in Progress, vol. 129, pp. 211–214. Oct. 1978.
Article: Complications and Difficulties i Electrocoagulation of Varices of the Lower Extremities. Politowski and Zelazny. Surgery, vol. 59, No. 6, pp. 932–934. Jun. 1966.
Article: Home Hemodialysis. The Medical Letter on Drugs and Therapeutics, No. 14, Issue 248, pp. 53–55. Jul. 1968.
Article: Tissue Heating During Radiofrequency Catheter Ablation: A Thermodynmaic Model and Observations in Isolated Perfused and Superfused Canine Right Ventricular Free Wall. Haines and Watson. Pace, vol. 12, pp. 962–975. Jun. 1989.

Primary Examiner—Lee S. Cohen

[57] ABSTRACT

A flexible bipolar electrode for neurosurgery includes an inner hypotube defining an irrigation passageway and a hollow outer electrode surrounding the hypotube, with the outer electrode and hypotube together establishing a bipolar electrode. An empty void is established between the electrodes to facilitate flexibility of the bipolar electrode when, for example, the electrode is advanced through a curved lumen of a neuroendoscopy instrument.

18 Claims, 2 Drawing Sheets

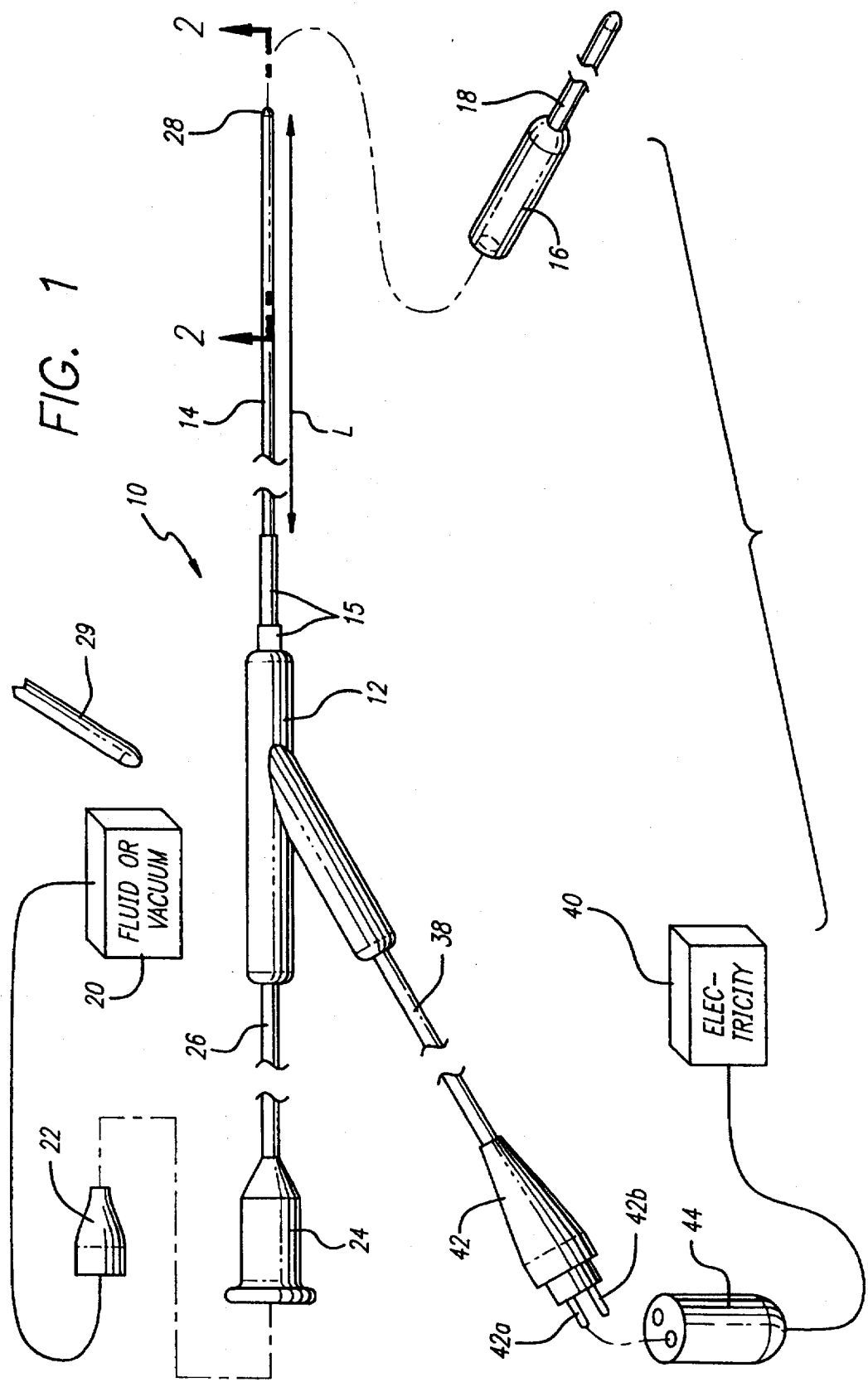

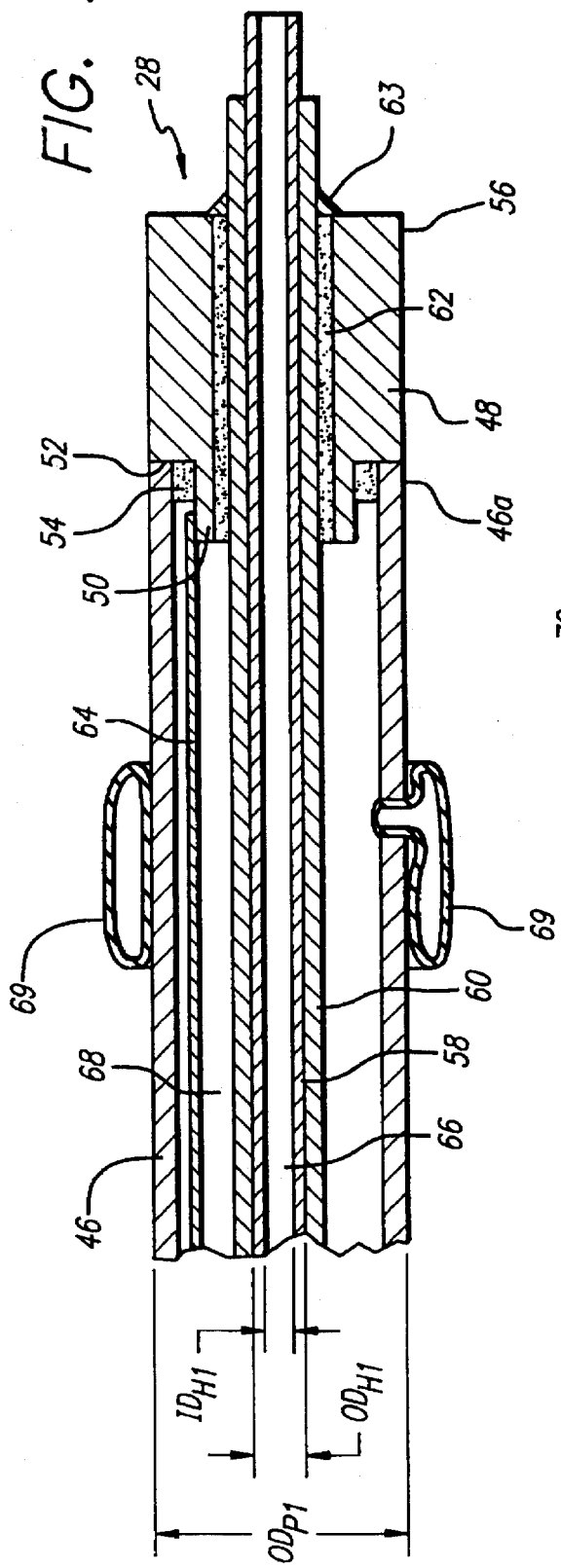
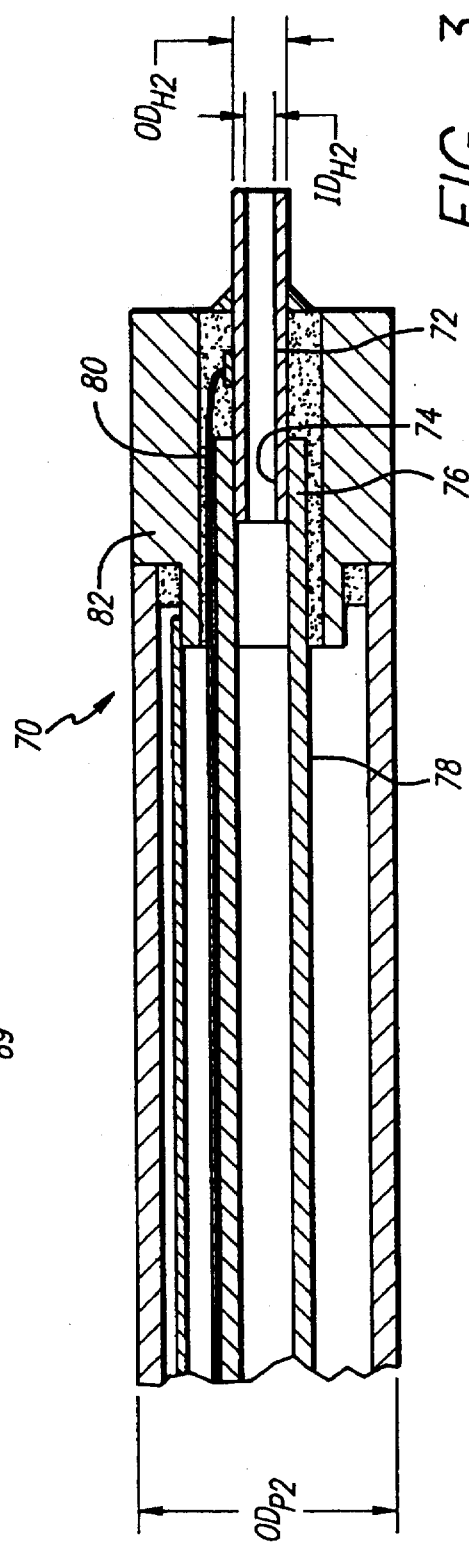

BIPOLAR ELECTRODE WITH FLUID CHANNELS FOR LESS INVASIVE NEUROSURGERY

FIELD OF THE INVENTION

The present invention relates generally to less invasive neurosurgery, and more particularly to electrodes for fenestrating and coagulating tissue during neurosurgery.

BACKGROUND

It is typically necessary to fenestrate (i.e., cut) tissue and to coagulate tissue during neurosurgery. It will readily be appreciated that when fenestration or coagulation of brain tissue is required, it is highly desirable to limit damage to tissue surrounding the area that is the target of the fenestration or coagulation, so as to minimize damage to the brain. It is also desirable to employ less invasive surgical techniques during neurosurgery, again to minimize damage to the brain and general trauma to the patient.

Accordingly, devices have been provided for precisely fenestrating and coagulating tissue. Such devices include electrodes having either one pole (referred to as monopolar electrodes) or two poles (referred to as bipolar electrodes). It happens that bipolar electrodes effect coagulation better than monopolar electrodes. Additionally, because the electrical path to ground in monopolar devices passes through substantial areas of the patient's body, monopolar devices cause considerable patient discomfort when, for example, the patient is lightly sedated in a so-called "twilight" sleep. Consequently, bipolar electrodes are preferred to monopolar electrodes for many neurosurgery applications.

Moreover, bipolar electrodes effect tissue coagulation better than many lasers, which might not necessarily operate at optimum wavelengths for tissue coagulation. Further, laser devices are comparatively more expensive than bipolar electrodes, and surgical personnel who use laser devices must be specially trained and certified before using the devices. Consequently, bipolar electrodes are preferred to lasers for many neurosurgery applications.

Not surprisingly, bipolar electrodes have been provided for tissue coagulation. An example of a bipolar device is disclosed in U.S. Pat. No. 4,674,499 to Pao, which teaches a bipolar electrode for eye surgery. As disclosed in Pao, a bipolar electrode is established by a hollow inner electrode and an outer electrode that is coaxial with the inner electrode. According to Pao, the space between the electrodes is entirely filled with insulation.

Accordingly, Pao provides only a single lumen for aspiration and irrigation. Also, because the space between the electrodes is entirely filled with insulation, the Pao device is relatively stiff. Unfortunately, while these drawbacks may not reduce the effectiveness of the Pao device when used for eye surgery, they render the Pao device difficult at best for use in neurosurgery applications, particularly in less invasive neurosurgery wherein a coagulation electrode may have to be advanced through a working channel of a flexible probe.

Accordingly, it is an object of the present invention to provide a flexible bipolar electrode for less invasive neurosurgery. Another object of the present invention is to provide a bipolar electrode for less invasive neurosurgery which establishes a pathway to a surgery site for irrigating fluid. Yet another object of the present invention is to provide a bipolar electrode for less invasive neurosurgery which is relatively flexible. Still another object of the present invention is to provide a bipolar electrode for less invasive neurosurgery which is easy to use and cost-effective.

SUMMARY OF THE INVENTION

A coagulation instrument for less invasive neurosurgery includes a flexible probe defining a distal end and a proximal end. As intended by the present invention, the probe includes an outer insulative sheath defining a distal end segment and an outer hollow cylindrical electrode engaged with the distal end segment of the outer sheath and coaxially disposed therewith. Further, an inner hollow electrode defines a fluid pathway therethrough. The inner electrode is disposed within the outer electrode and is coaxially oriented therewith such that a substantially empty void is established between the inner electrode and outer electrode.

Preferably, a conductive wire which includes silver interconnects at least one of the electrodes to a source of electricity. In the preferred embodiment, an insulative sheath is engaged with the inner electrode over a substantial length thereof. To insulate the inner electrode from the outer electrode, the insulative sheath is positioned between the void and the inner electrode. The insulative sheath, however, does not fill the void, thereby rendering the instrument relatively flexible.

Per the presently preferred embodiment, the outer electrode is formed with a disc-shaped collar which abuts the outer insulative sheath. Additionally, the outer electrode includes a cylindrical bonding segment extending proximally from the collar and bonded to the outer insulative sheath. Advantageously, the present instrument can be used in combination with a source of irrigating fluid which can be connected the fluid pathway.

In another aspect of the present invention, in combination with a source of irrigating fluid, a neurosurgery probe is disclosed which includes an outer hollow electrode defining a distal end. The probe also includes an inner hollow electrode assembly defining a distal end and further defining a fluid pathway from the distal end of the inner electrode to the source of irrigating fluid. The inner electrode assembly is coaxially disposed in the outer electrode such that an annular void is established between the inner electrode assembly and outer electrode.

In still another aspect of the present invention, a flexible bipolar electrode is disclosed for simultaneously fenestrating or coagulating tissue at a neurosurgery site while establishing a pathway between the neurosurgery site and one of: a source of irrigating fluid, a source of vacuum, a guidewire. The electrode includes a source of electricity and a hollow insulated hypotube defining a pathway therethrough. The hypotube is electrically connected to the source of electricity. A hollow insulated electrode is positioned around the hypotube and is radially distanced therefrom to establish a void therebetween. In accordance with the present invention, the electrode is electrically connected to the source of electricity and the pathway is operably engaged with one of the source of irrigating fluid, the source of vacuum, the guidewire.

In yet another aspect of the present invention, a coagulation and fenestration tool is disclosed which is advanceable through a lumen of a flexible neuroendoscope for neurosurgery. The present tool includes an outer cylindrical flexible electrode assembly and an inner flexible tubular electrode assembly. The inner assembly is disposed within the outer assembly coaxially therewith to thereby establish an empty void therebetween.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a perspective view of the bipolar electrode of the present invention, showing the sources of electricity, vacuum, and irrigating fluid schematically;

FIG. 2 is a cross-sectional view as seen along the line 2—2 in FIG. 1; and

FIG. 3 is a cross-sectional view of an alternate embodiment of the bipolar electrode, as would be along the line 2—2 in FIG. 1.

DETAILED DESCRIPTION OF THE PREFERRED EMBODIMENT

Referring initially to FIG. 1, a coagulation and fenestration tool for endoscopic neurosurgery is shown, generally designated 10. As shown, the tool 10 includes a rigid hollow plastic Y-shaped handle 12 and an elongated flexible probe 14 extending distally away from the handle 12. In the presently preferred embodiment, the probe 14 defines a length "L" of about ninety centimeters (90 cm), with the probe 14 extending into the handle 12 and being connected thereto and supported by a plurality of shrink tube segments 15 in accordance with principles well-known in the art.

As intended by the present invention, the probe 14 is "flexible" in that the probe 14 can be advanced through a flexible neuroendoscope 16 when a neuroendoscope probe 18 of the neuroendoscope 16 is bent to conform to an anatomical feature or to contact a blood vessel in or against which the neuroendoscope probe 18 is positioned. The neuroendoscope 16 can be one of the neuroendoscopes owned by the present assignee and disclosed in U.S. Pat. Nos. 5,318,526, 5,437,626, and 5,458,606, incorporated herein by reference.

As further disclosed below, the probe 14 defines a pathway for fluid communication which extends into the handle 12. As shown in FIG. 1, a source 20 of fluid or vacuum can be associated with a first luer fitting 22, and the first luer fitting 22 can be connected to a second luer fitting 24. In turn, the second luer fitting 24 is connected to the fluid pathway of the probe 14 within the handle 12 by means well-known in the art via a fluid line 26. Thereby, fluid communication from the source 20 of fluid or vacuum to a distal end 28 of the probe 14 is established. Alternatively, a guide wire 29 can be positioned in the fluid pathway disclosed below.

In addition to establishing a pathway for fluid communication as described, the probe 14 includes a bipolar electrode. Accordingly, an electrical line 38 is provided for conducting electricity from a source 40 of electricity to the bipolar electrode of the present invention. As shown, the electrical line 38 terminates in a dual-pin plug 42 having male elements 42a, 42b. The dual-pin plug 42 in turn mates with a complementary plug 44 that is associated with the source 40 of electricity. The electrical line 38 is engaged with the handle 12 by means well-known in the art, and it is to be understood that the electrical line 38 is electrically connected to the electrode elements of the bipolar electrode of the present invention as more fully disclosed below.

Per the present invention, the source 20 can be any suitable source of surgical irrigation fluid known in the art. Alternatively, the source 20 can be any well-known source of surgical aspiration vacuum known in the art. Also, the source 40 of electricity is a suitable source of surgical electrocautery current, e.g., a Bovie generator made by Valleylabs of Boulder, Colo.

Now referring to FIG. 2, the details of one presently preferred embodiment of the probe 14 can be seen. As shown, the probe 14 includes a flexible tubular electrically insulative outer sheath 46 which defines an outside diameter $OD_{P1}$ of about one millimeter (1 mm). Preferably, the outer sheath 46 is made of polyimide and extends substantially the length of the probe 14.

As shown in FIG. 2, the outer sheath 46 also defines a distal-most segment 46a. An electrically conductive, hollow, preferably stainless steel outer electrode tip 48 has a proximal bonding segment 50 that is engaged with the distal-most segment 46a of the outer sheath 46 coaxially therewith.

It is to be understood that the outer sheath 46 and outer electrode tip 48 together establish an outer electrode assembly. Because the outer electrode 48 does not extend the length of the probe 14, the outer electrode assembly is rendered flexible substantially throughout its length.

With particular regard to the outer electrode 48, the outer electrode 48 is formed with a disc-shaped collar 52 which abuts the distal-most segment 46a of the outer insulative sheath 46. Further, the bonding segment 50 of the outer electrode 48 extends proximally from the collar 52 and is bonded to the outer insulative sheath 46 by means of an epoxy adhesive 54. The radial dimension of the cylindrical proximal bonding segment 50 is smaller than the radial dimension of a cylindrical distal segment 56 of the outer electrode 48. Indeed, as shown the distal segment 56 of the outer electrode 48 defines a diameter that is substantially equal to the diameter $OD_{P1}$ of the outer sheath 46. Consequently, as shown the outer surface of the distal segment 56 is substantially flush with the outer surface of the outer sheath 46.

An elongated, electrically conductive hollow inner electrode 58 extends through the outer electrode assembly of the present invention, substantially coaxially therewith. Preferably, the inner electrode 58 is a stainless steel hypotube having an inside diameter $ID_{H1}$ of about ten thousandths of an inch (0.010") and an outside diameter $OD_{H1}$ of about twenty thousandths of an inch (0.020"). More preferably, the outside diameter $OD_{H1}$ of the inner electrode 58 is about sixteen thousandths of an inch (0.016").

To electrically insulate the inner electrode 58, an inner electrically insulative, preferably etched Teflon® sheath 60 surrounds the inner electrode 58 and is bonded thereto. It is to be understood that the inner sheath 60 can be deposited directly onto the inner electrode 58. Together, the inner electrode 58 and inner sheath 60 establish an inner electrode assembly that extends substantially the length of the probe 14, coaxially with the outer electrode assembly. We have discovered that owing to its above-disclosed configuration, the inner electrode 58 is rendered flexible substantially throughout its length.

As can be appreciated in reference to FIG. 2. the inner electrode assembly is radially supported by a cylindrical epoxy adhesive layer 62 which is sandwiched between the outer electrode 48 and the inner sheath 60. As shown, the inner electrode assembly extends distally beyond the outer electrode 48, with the inner electrode 58 extending marginally distally further than the inner sheath 60. Ultraviolet adhesive 63 is deposited at the distal end of the epoxy adhesive layer 62 as shown.

To energize the outer electrode 48, a conductive wire 64 is soldered to the outer electrode 48, and it is to be understood that the wire 64 is electrically connected to the male element 42a of the dual-pin plug 42 (FIG. 1) by means well-known in the art. In the presently preferred embodiment, the wire 64 is a polyimide-insulated low-resistance drawn-filled tube having a silver core surrounded by a stainless steel sheath.

On the other hand, the inner electrode 58 extends through the probe 14, and is electrically connected to the male element 42b of the plug 42 within the handle 12. The skilled artisan will accordingly recognize that the electrodes 48, 58 establish a bipolar electrode that can be used for fenestration and coagulation of tissue by appropriately energizing the source 40 of electricity.

Further, it may now be appreciated that the probe 14 establishes a pathway for fluid communication through the probe 14 to its distal end 28. More specifically, a pathway 66 for fluid communication is established by the hollow inner electrode 58, and the pathway 66 is substantially empty when fluid does not communicate through it. Within the handle 12, the pathway 66 is connected to the fluid line 26 shown in FIG. 1 to establish fluid communication between the source 20 of fluid or vacuum and the distal end 28 of the probe 14.

Moreover, an annular void 68 is established between the inner electrode assembly and the outer electrode assembly, and the wire 64 extends through the void 68. It is to be understood that the void 68 is empty of insulation or other solid material (except for the wire 64). As a consequence, the probe 14 is not unduly stiffened as it otherwise would be by the presence of solid material in the void 68. If desired, an inflatable angioplasty balloon 69 can be disposed on the outer sheath 46 in a surrounding relationship thereto and in fluid communication with the void 68. Fluid can be directed through the void 68 into the balloon 69 to inflate the balloon 69 in accordance with angioplasty procedures known in the art.

In the operation of the tool 10, the probe 14 can be advanced into the brain of a patient through, e.g., the neuroendoscope probe 18 (FIG. 1). Then, the source 40 of electricity can be activated to cause the cooperation of the electrodes 48, 58 to fenestrate and/or coagulate tissue. Fluid from the source 20 of fluid can be directed through the pathway 66 to irrigate the surgical site during fenestration/coagulation. Or, the source 20 can be a source of vacuum, and the surgical site can be aspirated through the pathway 66 by activating the source 20.

Advantageously, when it is desired to fenestrate a membrane without damaging a blood vessel that may be located behind the membrane, the source 20 is a source of vacuum. The distal end 28 of the probe 14 can be gently advanced against the membrane, and then retracted a short distance, with the vacuum in the pathway 66 pulling the membrane away from the blood vessel. Next, the electrodes 48, 58 can be energized to fenestrate the membrane. It will be appreciated that with the cooperation of structure just described, the likelihood of inadvertently damaging the blood vessel behind the membrane is reduced, compared with what it otherwise would be if the membrane were to be pierced by pushing a mechanical puncturing tool through the membrane.

FIG. 3 shows a probe, generally designated 70, which is substantially identical in configuration and operation to the probe 14 shown in FIG. 2, with the following exceptions. The outside diameter $OD_{P2}$ of the probe 70 shown in FIG. 3 is about two and three-tenths millimeters (2.3 mm). Further, an inner electrode 72 is established by a hypotube defining an inside diameter $ID_{H2}$ of about twenty seven thousandths of an inch (0.027") and an outside diameter $OD_{H2}$ of about forty two thousandths of an inch (0.042").

Because of its relative stiffness owing to its relatively large diameter vis-a-vis the inner electrode 58 shown in FIG. 2, the electrode 72 shown in FIG. 3 is configured so that it does not extend substantially the length of the probe 70. Instead, the inner electrode 72 defines a proximal segment 74 that is bonded to a distal-most segment 76 of an inner insulative, preferably polyimide, sheath 78. In accordance with principles discussed above, the inner electrode 72 and inner sheath 78 establish an inner electrode assembly which is flexible. With this combination of structure, the probe 70 is not unduly stiffened, but is rendered relatively flexible.

A conductive wire 80 which is in all essential respects identical in configuration and construction to the wire 64 shown in FIG. 2 electrically connects the inner electrode 72 to a source of electricity. Also, in contrast to the inner sheath 60 shown in FIG. 2, the inner sheath 78 shown in FIG. 3 does not extend distally beyond an outer electrode 82 of the probe 70. The probe 70 shown in FIG. 3 is otherwise identical to the probe 14 shown in FIG. 2.

While the particular BIPOLAR ELECTRODE WITH FLUID CHANNELS FOR LESS INVASIVE NEUROSURGERY as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A coagulation instrument for less invasive neurosurgery, comprising:
    a flexible probe defining a distal end and a proximal end, the probe including:
    an outer insulative sheath defining a distal end segment;
    an outer hollow cylindrical electrode engaged with the distal end segments of the outer sheath and coaxially disposed therewith; and
    an outer hollow electrode assembly defining a fluid pathway therethrough, the inner electrode assembly including an inner electrode established by a hypotube defining an outside diameter of less than about twenty thousandths of an inch (0.020"), the inner electrode assembly being dispopsed within the outer electrode and coaxially oriented therewith such that a substantially empyt void is establihed between the inner electrode assembly and the outer electrode.

2. The instrument of claim 1, further comprising a conductive wire including silver, the conductive wire being connected to one of the electrodes.

3. The instrument of claim 2, wherein the inner electrode assembly includes an insulative sheath engaged with the inner electrode over a substantial length thereof, the insulative sheath being positioned between the void and the inner electrode.

4. The instrument of claim 3, wherein the outer electrode is formed with a disc-shaped collar abutting the outer insulative sheath and a cylindrical bonding segment extending proximally from the collar and bonded to the outer insulative sheath.

5. The instrument of claim 4, in combination with:
    a source of irrigating fluid connected to the fluid pathway.

6. In combination with a source of irrigating fluid, a neurosurgery probe, comprising:

an outer hollow electrode defining a distal end; and an inner hollow electrode assembly defining a distal end and further defining a fluid pathway from the distal end of the inner electrode assembly to the source of irrigating fluid, the inner electrode assembly being coaxially disposed in the outer electrode such that an annular empty void is established between the inner electrode assembly and outer electrode to render the probe flexible, the inner electrode assembly including an inner electrode established by a hypotube defining an outside diameter of less than about twenty thousandths of an inch (0.020").

7. The probe of claim 6, further comprising an outer insulative sheath at least partially surrounding the outer electrode.

8. The probe of claim 7, further comprising a conductive wire including silver, the conductive wire being connected to the outer electrode.

9. The probe of claim 8, wherein the inner electrode assembly includes an insulative sheath engaged with the inner electrode over a substantial length thereof, the insulative sheath being positioned between the annular void and the inner electrode.

10. The probe of claim 9, wherein the outer electrode is formed with a disc-shaped collar abutting the outer insulative sheath and a cylindrical bonding segment extending proximally from the collar and bonded to the outer insulative sheath.

11. The probe of claim 10, further comprising an inflatable balloon positioned on the outer sheath in fluid communication with the void.

12. A flexible bipolar electrode for simultaneously fenestrating or coagulating tissue at a neurosurgery site while establishing a pathway between the neurosurgery site and one of: a source of irrigating fluid, a source of vacuum, a guidewire, the bipolar electrode comprising:

a source of electricity;

a hollow insulated hypotube defining a pathway therethrough, the hypotube being electrically connected to the source of electricity, the hypotube defining an outside diameter of less than about twenty thousandths of an inch (0.020"); and a hollow, at least partially insulated electrode positioned around the hypotube and radially distanced therefrom to establish a void therebetween, the electrode being electrically connected to the source of electricity and the pathway being operably engaged with one of the source of irrigating fluid, the source of vacuum, the guidewire.

13. The electrode of claim 12, wherein the electrode is insulated by an outer insulative sheath at least partially surrounding the electrode.

14. The electrode of claim 13, further comprising a conductive wire including silver, the conductive wire being connected to one of the electrode and the hypotube.

15. The electrode of claim 14, wherein the hypotube is insulated by an insulative sheath engaged with the hypotube over a substantial length thereof, the insulative sheath being positioned between the void and the hypotube.

16. The electrode of claim 15, wherein the electrode is formed with a disc-shaped collar abutting the outer insulative sheath and a cylindrical bonding segment extending proximally from the collar and bonded to the outer insulative sheath.

17. A coagulation and fenestration tool advanceable through a lumen of a flexible neuroendoscope for neurosurgery, comprising:

an outer cylindrical flexible electrode assembly establishing a first electrode; and an inner flexible tubular electrode assembly disposed within the outer assembly coaxially therewith to thereby establish a pathway for fluid communication therebetween, the inner electrode assembly including:

a flexible tubular insulative inner sheath extending substantially the length of the inner flexible tubular electrode assembly; and a metal hypotube disposed within the inner sheath coaxially therewith and extending substantially the length of the inner flexible tubular electrode assembly to establish a second electrode, the hypotube defining an outside diameter of less than about twenty thousandths of an inch (0.020") to thereby render the inner electrode assembly flexible.

18. The tool of claim 17, wherein the electrode assemblies establish an elongated flexible probe, and the outer electrode assembly includes:

an outer flexible insulative sheath defining a distal-most segment, the outer sheath extending substantially the length of the probe; and a metal tip having a proximal segment attached to the distal-most segment of the outer sheath to thereby render the outer electrode assembly flexible substantially throughout its length, the metal tip establishing an outer electrode.

* * * * *